(12) United States Patent
Wang et al.

(10) Patent No.: US 9,273,215 B2
(45) Date of Patent: Mar. 1, 2016

(54) ADHESION PROMOTER

(71) Applicant: Rohm and Haas Electronic Materials LLC, Marlborough, MA (US)

(72) Inventors: Zidong Wang, Southborough, MA (US); Michael K. Gallagher, Hopkinton, MA (US); Kevin Y. Wang, Shrewsbury, MA (US); Gregory P. Prokopowicz, Worcester, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 250 days.

(21) Appl. No.: 14/062,677

(22) Filed: Oct. 24, 2013

(65) Prior Publication Data

US 2014/0120244 A1  May 1, 2014

Related U.S. Application Data

(63) Continuation-in-part of application No. 13/664,337, filed on Oct. 30, 2012.

(51) Int. Cl.
| | |
|---|---|
| *B05D 5/12* | (2006.01) |
| *C09D 7/12* | (2006.01) |
| *C07F 7/08* | (2006.01) |
| *C08F 32/00* | (2006.01) |
| *C09D 165/02* | (2006.01) |
| *C08K 5/544* | (2006.01) |
| *C08L 65/00* | (2006.01) |
| *H01L 21/02* | (2006.01) |
| *C09D 165/00* | (2006.01) |
| *C09D 183/14* | (2006.01) |
| *C08G 77/48* | (2006.01) |
| *C08G 77/50* | (2006.01) |

(52) U.S. Cl.
CPC ............ *C09D 7/1233* (2013.01); *C07F 7/0805* (2013.01); *C08F 32/00* (2013.01); *C08K 5/544* (2013.01); *C08L 65/00* (2013.01); *C09D 165/00* (2013.01); *C09D 165/02* (2013.01); *C09D 183/14* (2013.01); *H01L 21/02118* (2013.01); *H01L 21/02282* (2013.01); *H01L 21/02304* (2013.01); *C08G 77/48* (2013.01); *C08G 77/50* (2013.01); *C08G 2261/3324* (2013.01); *C08G 2261/3325* (2013.01); *C08G 2261/3422* (2013.01); *C08G 2261/418* (2013.01)

(58) Field of Classification Search
USPC ........................................................... 427/58
See application file for complete search history.

(56) References Cited

U.S. PATENT DOCUMENTS

| | | | |
|---|---|---|---|
| 5,668,210 A | 9/1997 | Harris et al. | |
| 5,994,489 A * | 11/1999 | Harris .................. | C09D 183/04 528/12 |
| 6,184,284 B1 | 2/2001 | Stokich, Jr. et al. | |
| 2006/0069171 A1 | 3/2006 | Prokopowicz et al. | |
| 2006/0147730 A1 | 7/2006 | O'Connell et al. | |

FOREIGN PATENT DOCUMENTS

| | | |
|---|---|---|
| JP | 5128574 B2 | 11/2012 |
| WO | 0038844 A1 | 7/2000 |

OTHER PUBLICATIONS

European Search Report of corresponding European Application No. 13 19 0432.
Co-Pending U.S. Appl. No. 14/062,677, filed Oct. 24, 2013.
J.M. Snodgrass et al.; "Subcritical debonding of polymer/silica interfaces under monotonic and cyclic loading"; Acta Materialia 50 (2002); pp. 2395-2411.
Search Report corresponds with China Application No. 201310753600.0 dated Dec. 12, 2014.
Search Report corresponds with Taiwan Application No. 102139034 dated Dec. 22, 2014.

\* cited by examiner

*Primary Examiner* — Austin Murata
(74) *Attorney, Agent, or Firm* — S. Matthew Cairns

(57) ABSTRACT

Compositions useful for improving the adhesion of coating compositions, such as dielectric film-forming compositions, include a hydrolyzed poly(alkoxysilane). These compositions are useful in methods of improving the adhesion of coating compositions to a substrate.

16 Claims, No Drawings

ADHESION PROMOTER

This application is a Continuation-in-Part of U.S. Non-Provisional application Ser. No. 13/664,337, filed on Oct. 30, 2012.

The present invention relates to the field of coating compositions and more particularly to a solution for improving the adhesion of certain coating compositions to a substrate.

Coating compositions are widely used in the electronics industry to deposit various organic-containing materials, such as polymeric materials, on a variety of substrates. Often the substrates are inorganic or have inorganic areas on the surface to be coated. For example, coating compositions such as dielectric film-forming compositions and bonding or adhesive compositions are often applied to glass, metal surfaces, and/or semiconductor surfaces such as silicon, gallium-arsenide, and silicon-germanium. Many organic materials do not adhere well to substrates having inorganic surfaces because they do not contain groups that have an affinity for such surfaces. Accordingly, it is common practice to treat such substrate surfaces with an adhesion promoter prior to disposing an organic-containing coating composition on it. Silanes are among the more common adhesion promoters used industrially.

Arylcyclobutene-based materials have been used in a wide variety of applications in the electronics industry due to their superior dielectric properties, excellent gap-fill and planarization, and low moisture adsorption. To use arylcyclobutene materials in applications such as interlevel dielectrics and wafer bonding applications, adequate adhesion of the arylcyclobutene material to various substrates (such as silicon, silicon nitride, gold, and copper) is required. Arylcyclobutene materials by themselves do not possess sufficient adhesion to these substrates, and therefore, an adhesion promoter is usually applied to enhance adhesion prior to coating the arylcyclobutene material.

Various adhesion promoters are known for use with arylcyclobutenes. For example, U.S. Pat. No. 5,668,210 discloses certain alkoxysilanes as adhesion promoters for arylcyclobutenes. Only monosilanes are disclosed in this patent. These alkoxysilanes are hydrolyzed with 10 to 80% of the stoichiometric amount (that is mole %) of water. However, conventional adhesion promoters are not able to meet the increasing requirements of the electronics industry for smaller feature sizes (<10 μm) and more complex chip designs, often resulting in delamination or other adhesive failures.

There remains a need for adhesion promoters that enable the use of arylcyclobutanes, as well as other organic coatings, with smaller feature sizes (<10 μm) and more complex chip designs. The present invention addresses one or more of these deficiencies.

The present invention provides a process of manufacturing a device, comprising: providing a device substrate having a surface to be coated; treating the surface to be coated with an adhesion promoting composition comprising an poly(alkoxysilane) and a solvent, wherein the poly(alkoxysilane) is hydrolyzed with ≤1 mole % of water, and wherein the composition comprises ≤1 mole % of alcohol of hydrolysis; and disposing a coating composition comprising an oligomer chosen from polyarylene oligomers, poly(cyclic-olefin) oligomers, arylcyclobutene oligomers, vinyl aromatic oligomers, and mixtures thereof on the treated surface. It is preferred that the device substrate is an electronic device substrate.

Also provided by the present invention is an adhesion promoting composition comprising: an oligomer chosen from polyarylene oligomers, poly(cyclic-olefin) oligomers, arylcyclobutene oligomers, and mixtures thereof; a poly(alkoxysilane) hydrolyzed with ≤1 mole % of water; and a solvent; wherein the composition comprises ≤1 mole % of alcohol of hydrolysis. Preferably, the composition has a mean particle size ≤1 nm as determined by dynamic light scattering.

Further, the present invention provides a method of manufacturing a device, comprising: providing a device substrate having a surface to be coated; and depositing a composition comprising: an oligomer chosen from polyarylene oligomers, poly(cyclic-olefin) oligomers, arylcyclobutene oligomers, vinyl aromatic oligomers, and mixtures thereof; and poly(alkoxysilane) hydrolyzed with ≤1 mole % of water; and a solvent; wherein the composition comprises ≤1 mole % of alcohol of hydrolysis.

It has been surprisingly found that poly(alkoxysilanes) hydrolyzed with ≤1 mole % of water are particularly effective adhesion promoters for coating oligomers chosen from polyarylene oligomers, poly(cyclic-olefin) oligomers, arylcyclobutene oligomers, vinyl aromatic oligomers, and mixtures thereof used in the manufacture of electronic devices. Such coating oligomers are useful in preparing dielectric coatings, photodefinable coatings, temporary bonding adhesives, and permanent bonding adhesives, among other applications.

As used throughout this specification, the following abbreviations shall have the following meanings, unless the context clearly indicates otherwise: ° C.=degrees Celsius; g=grams; L=liter; mL=milliliters; ppm=parts per million; mm=millimeters; μm=micron=micrometers; nm=nanometers; and Å=angstroms. "Wt %" refers to percent by weight, based on the total weight of a referenced composition, unless otherwise noted. All amounts are percent by weight and all ratios are molar ratios, unless otherwise noted. All numerical ranges are inclusive and combinable in any order, except where it is clear that such numerical ranges are constrained to add up to 100%. The articles "a", "an" and "the" refer to the singular and the plural.

As used throughout the specification, "feature" refers to the geometries on a substrate, and particularly on a semiconductive wafer. The term "alkyl" includes linear, branched and cyclic alkyl. Likewise, "alkenyl" refers to linear, branched and cyclic alkenyl. "Aryl" refers to aromatic carbocycles and aromatic heterocycles. The term "oligomer" refers to dimers, trimers, tetramers and other relatively low molecular weight materials that are capable of further curing. By the term "curing" is meant any process, such as polymerization or condensation, that increases the molecular weight of a material or composition.

The poly(alkoxysilanes) useful in the present invention are composed of at least two alkoxysilane moieties, that is, moieties represented by —Si(Z)$_2$OR$^1$. Preferably, the poly(alkoxysilanes) have from 2 to 6 alkoxysilane moieties, more preferably from 2 to 4 alkoxysilane moieties, even more preferably from 2 to 3 alkoxysilane moieties; and most preferably 2 alkoxysilane moieties. As used herein, the term "alkoxysilane" moiety includes silane moieties substituted with one or more ($C_1$-$C_6$)alkoxy groups and/or one or more ($C_1$-$C_6$)acyloxy groups. Preferably, each alkoxysilane moiety comprises three ($C_1$-$C_6$)alkoxy groups and/or ($C_1$-$C_6$)acyloxy groups, and more preferably three ($C_1$-$C_6$)alkoxy groups.

Particularly preferred poly(alkoxysilanes) prior to being hydrolyzed have the formula:

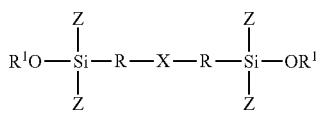

wherein each R is independently chosen from $(C_1-C_6)$alkylidene, $(C_1-C_6)$alkylene, $(C_6-C_{10})$arylene, and $(C_2-C_6)$alkenylene; each $R^1$ is independently chosen from H, $(C_1-C_6)$alkyl and $(C_1-C_6)$acyl; each Z is independently chosen from $(C_1-C_6)$alkyl, $(C_2-C_6)$alkenyl and —$OR^1$; X=$(C_6-C_{10})$arylene, O, S, S—S, S—S—S, S—S—S—S, N(Y), P(Y) or a covalent bond; Y=H, $(C_1-C_6)$alkyl, $(C_1-C_6)$alkylene-N$(Y^1)_2$, $(C_2-C_6)$alkenyl, $(C_1-C_6)$alkylene-Si(Z)$_2$(OR$^1$), $(C_1-C_6)$alkylidene-Si(Z)$_2$(OR$^1$), or aryl(meth)acryloyl; and $Y^1$=H, $(C_1-C_6)$alkyl, or $(C_2-C_6)$alkenyl; wherein each R is optionally substituted with one or more of $(C_1-C_6)$alkylidene-Si(Z)$_2$(OR$^1$) and $(C_1-C_6)$alkylene-Si(Z)$_2$(OR$^1$). Each R is preferably independently chosen from $(C_1-C_6)$alkylidene, $(C_1-C_6)$alkylene, and $(C_2-C_6)$alkenylene, each optionally substituted with one or more of $(C_1-C_6)$alkylidene-Si(Z)$_2$(OR$^1$) and $(C_1-C_6)$alkylene-Si(Z)$_2$(OR$^1$). More preferably, each R is independently chosen from $(C_2-C_6)$alkylidene, $(C_2-C_6)$alkylene, and $(C_2-C_6)$alkenylene. When an R group is substituted with $(C_1-C_6)$alkylidene-Si(Z)$_2$(OR$^1$) or $(C_1-C_6)$alkylene-Si(Z)$_2$(OR$^1$), it is preferred that 1 to 2 of such groups are present. Each $R^1$ is preferably chosen from $(C_1-C_4)$alkyl and $(C_2-C_6)$acyl; and more preferably from $(C_1-C_3)$alkyl and $(C_2-C_4)$acyl. It is preferred that each Z is chosen from $(C_1-C_4)$alkyl, $(C_2-C_6)$alkenyl and —$OR^1$; and more preferably each Z is —$OR^1$. Preferably, X is chosen from S—S, S—S—S, S—S—S—S, N(Y), or a covalent bond, and more preferably from N(Y) or a covalent bond. It is preferred that Y is chosen from H, $(C_1-C_4)$alkyl, $(C_1-C_4)$alkylene-N$(Y^1)_2$, $(C_2-C_6)$alkenyl, $(C_2-C_6)$alkylene-Si(Z)$_2$(OR$^1$), and aryl(meth)acryloyl; and more preferably from H, $(C_2-C_4)$alkylene-N$(Y^1)_2$, $(C_2-C_4)$alkenyl, $(C_2-C_4)$alkylene-Si(Z)$_2$(OR$^1$), and aryl(meth)acryloyl. $Y^1$ is preferably chosen from H, $(C_1-C_4)$alkyl, or $(C_2-C_4)$alkenyl; and more preferably from H, and $(C_1-C_4)$alkyl. Suitable poly(alkoxysilanes) are commercially available from a variety of sources, such as Sigma-Aldrich (St. Louis, Mo.), or may be prepared by any suitable method known in the literature. The poly(alkoxysilanes) may be used without further purification, or may be purified using suitable conventional procedures.

Conventional alkoxysilane adhesion promoters use a large amount of water (close to a stoichiometric amount) to partially or fully hydrolyze the alkoxysilanes. To achieve complete (100%) hydrolysis, a stoichiometric amount of water is 1 molar equivalent of water for each molar equivalent of alkoxy (or acyloxy) group present on each alkoxysilane moiety. In practice, somewhat less than a stoichiometric amount of water is required for complete hydrolysis since water is formed by condensation reactions during the hydrolysis. Accordingly, conventional adhesion promoters typically use from 10 to 80% of the stoichiometric amount of water. In comparison, the poly(alkoxysilanes) of the present invention are partially hydrolyzed using very small amounts of water, that is much less than a stoichiometric amount of water. To be useful in the present invention, the poly(alkoxysilanes) are hydrolyzed with ≤1 mole % of water, preferably ≤0.5 mole %, and more preferably ≤0.3 mole %. A suitable amount of water for such hydrolysis is from 0.0001 to 1 mole %, preferably from 0.001 to 1 mole %, more preferably from 0.001 to 0.5 mole %, even more preferably from 0.01 to 0.5 mole %. The water used in the hydrolysis should be purified, and preferably is deionized. As a result of this hydrolysis, an alcohol of hydrolysis is formed, which is the alcohol formed from cleavage of an alkoxy group from the silane moiety. For example, cleavage of an ethoxy group from a triethoxysilane moiety results in the formation of ethanol as the alcohol of hydrolysis. As a further example, hydrolysis of a triacetoxysilane moiety results in the formation of acetic acid as the "alcohol" of hydrolysis. The amount of alcohol of hydrolysis resulting from the present poly(alkoxysilane) hydrolysis is ≤1 mole %, preferably ≤0.5 mole %, and more preferably ≤0.3 mole %.

The poly(alkoxysilanes) may be hydrolyzed according to procedures known in the art, such as where the poly(alkoxysilane) is contacted with a desired amount of water, or by contacting the poly(alkoxysilane) with water in the presence of a volatile solvent, or by simply combining the poly(alkoxysilane) with a suitable solvent where the solvent has sufficient residual water content to effect the desired level of hydrolysis. If a volatile solvent (or solvent mixture) is used, it is optionally removed prior to the hydrolyzed poly(alkoxysilane) being incorporated into the present coating composition. In one preferred process, the hydrolysis is performed by combining the poly(alkoxysilane) with a suitable organic solvent having sufficient residual water to effect the desired level of hydrolysis. In another preferred process, a desired amount of water is first combined with a desired solvent, and then this mixture is combined with the poly(alkoxysilane). Optionally, an acidic or basic catalyst may be employed in the hydrolysis reaction, but it is preferred that no catalyst be used.

The optional acidic or basic catalysts may be any acidic or basic compound which will catalyze the hydrolysis of the poly(alkoxysilane). Examples of acidic catalysts include but are not limited to nitric acid, hydrochloric acid, sulfuric acid, trifluoroacetic acid, chloroacetic acid, methane sulfonic acid, and phosphoric acid. Examples of basic catalysts include but are not limited to potassium hydroxide, sodium hydroxide, ammonium hydroxide, tetramethylammonium hydroxide, and tetraethylammonium hydroxide. When present, the catalyst is used in amounts sufficient to catalyze the hydrolysis reaction. The amount of catalyst advantageously employed will depend upon a number of factors including the desired rate of hydrolysis, the catalyst, the poly(alkoxysilane) used, and the degree of hydrolysis desired. Preferably, the catalyst is present in amounts from 0 ppm to 50 ppm based on the amount of poly(alkoxysilane). More preferably, the catalyst is present in amounts from 0 ppm to 100 ppm and most preferably from 0 ppm to 30 ppm, based on the amount of poly(alkoxysilane).

While not wishing to be bound by theory, it is believed that hydrolysis of poly(alkoxysilanes) produces a mixture of non-hydrolyzed, partially hydrolyzed, fully hydrolyzed and oligomerized poly(alkoxysilanes). Oligomerization occurs when a hydrolyzed or partially hydrolyzed poly(alkoxysilane) reacts with another poly(alkoxysilane) to produce water and an Si—O—Si bond. As used herein, the term "hydrolyzed poly(alkoxysilane)" encompasses all level of hydrolysis of the poly(alkoxysilane), as well as oligomerized poly(alkoxysilane). Also as used herein, the term "poly(alkoxysilane) and/or hydrolyzed poly(alkoxysilane)" refers to a poly(alkoxysilane), or a hydrolyzed poly(alkoxysilane), or a mixture of these.

In the hydrolysis reaction, the poly(alkoxysilane), water, solvent, and optional catalyst are mixed until the desired hydrolysis is complete. While the time to complete the hydrolysis will vary depending on a number of factors, including the specific reactants employed and the level of hydrolysis desired, in general, the hydrolysis is complete in 2 minutes to 5 hours, preferably from 4 minutes to 2 hours, and more preferably from 10 minutes to 1 hour. In general, because of the very low levels of water used, the poly(alkoxysilane), water, and solvent will form a single-phase mixture. In general, the mixture is agitated for 1 minute to 2 hours after a single phase is obtained to complete the hydrolysis reaction. The temperature at which hydrolysis is conducted is preferably from about 15 to 100° C., more preferably from 20 to 50° C., and most preferably from 20 to 25° C. Hydrolysis rates increase with increasing temperatures. Preferably, the hydrolysis is conducted in the absence of a catalyst. In such procedure, the desired amount of water is mixed with the desired solvent, then combined with the poly(alkoxysilane) and stirred for a sufficient period of time for the desired extent of hydrolysis to occur. Preferably, the solvent used is the same solvent used to prepare the treating (adhesion promoter) composition. This method may take up to several days dependent upon the poly(alkoxysilane) and the temperature at which hydrolysis occurs. In some applications this method may be preferred when residual catalyst levels have an adverse effect on subsequent use of the poly(alkoxysilane).

The present adhesion promoter compositions comprise a poly(alkoxysilane) hydrolyzed with ≤1 mole % of water and a solvent; wherein the composition comprises ≤1 mole % of alcohol of hydrolysis. The solvent used in the adhesion promoting composition of the present invention can be any single organic solvent or mixture of two or more organic solvents in which the hydrolyzed poly(alkoxysilane) is soluble. Exemplary organic solvents include, without limitation: aromatic hydrocarbons such as toluene, xylene, mesitylene and alkylnaphthalenes; alcohols such as 2-methyl-1-butanol, 4-methyl-2-pentanol, and methyl isobutyl carbinol; esters such as ethyl lactate, propylene glycol methyl ether acetate (PGMEA), and methyl 2-hydroxyisobutyrate; lactones such as gamma-butyrolactone; lactams such as N-methylpyrrolidinone; ethers such as anisole, propylene glycol methyl ether and dipropylene glycol dimethyl ether isomers (commercially available from The Dow Chemical Company as Proglyde™ DMM); ketones such as cyclohexanone and methylcyclohexanone; and mixtures thereof.

In general, the present adhesion promoter compositions comprise from 0.01 to 10 wt % of poly(alkoxysilane) and/or hydrolyzed poly(alkoxysilane), and from 90 to 99.99 wt % of solvent. Preferably, the adhesion promoter compositions comprise form 0.01 to 5 wt % of poly(alkoxysilane) and/or hydrolyzed poly(alkoxysilane), more preferably from 0.01 to 3 wt %, and even more preferably from 0.01 to 2 wt %. Preferably, the adhesion promoter compositions comprise from 90 to 99.95 wt % of solvent, more preferably from 95 to 99.95 wt %, and even more preferably from 98 to 99.9 wt %. Particularly preferred compositions comprise from 0.05 to 3 wt % of poly(alkoxysilane) and/or hydrolyzed poly(alkoxysilane), and from 97 to 99.95 wt % of solvent.

The present adhesion promoter compositions are typically applied to an electronic device substrate to improve the adhesion of subsequently applied coating compositions. The present process of manufacturing a device, comprises: providing a device substrate having a surface to be coated; treating the surface to be coated with a composition comprising an poly(alkoxysilane) and a solvent, wherein the poly(alkoxysilane) is hydrolyzed with ≤1 mole % of water, and wherein the composition comprises ≤1 mole % of alcohol of hydrolysis; and disposing a composition comprising an oligomer chosen from polyarylene oligomers, poly(cyclic-olefin) oligomers, arylcyclobutene oligomers, vinyl aromatic oligomers, and mixtures thereof on the treated surface.

The device may be any suitable substrate used in the manufacture of electronic devices, including, without limitation: packaging substrates such as multichip modules; flat panel display substrates; integrated circuit substrates, substrates for light emitting diodes (LEDs), semiconductor wafers, polycrystalline silicon substrates, and the like. Exemplary device substrates which can be coated with the coating composition include metals such as aluminum, copper, gold, silver, titanium, tantalum, nickel, tin, tin-alloys, and the like; ceramics such as alumina, silica, sapphire, MgO, BeO, including spinels, aluminum nitride, boron nitride, silicon nitride, silicon carbide, and gallium arsenide; glass such as fiber glass, lime glass, flint glass, borosilicate glass, Gorilla™ glass, Pyrex™ glass and Vycor™ glass; and semiconductor wafers. A wide variety of semiconductor wafers may be employed in the present invention. As used herein, the term "semiconductor wafer" is intended to encompass "an electronic device substrate," "a semiconductor substrate," "a semiconductor device," and various packages for various levels of interconnection, including a single-chip wafer, multiple-chip wafer, packages for various levels, or other assemblies requiring solder connections. Particularly suitable substrates are patterned wafers, such as patterned silicon wafers and patterned gallium-arsenide wafers. Such wafers may be any suitable size. Preferred wafer diameters are 200 mm to 300 mm, although wafers having smaller and larger diameters may be suitably employed according to the present invention. As used herein, the term "semiconductive substrates" includes any substrate having one or more semiconductor layers or structures which include active or operable portions of semiconductor devices. The term "semiconductor substrate" is defined to mean any construction comprising semiconductive material, including but not limited to bulk semiconductive material such as a semiconductive wafer, either alone or in assemblies comprising other materials thereon, and semiconductive material layers, either alone or in assemblies comprising other materials. A semiconductor device refers to a semiconductor substrate upon which at least one microelectronic device has been or is being batch fabricated. Preferably, if the substrate is a metal such as copper, it is treated with an etchant such as 1% acetic acid prior to application of the coating composition. Substrates commonly used in high density electronic circuitry, such as silicon, thermally oxidized silicon, GaAs, alumina and aluminum are commonly treated by processes such as oxygen plasma etching or RCA clean, to control surface chemistry.

The device substrate surface is treated by contacting the device substrate surface with the present adhesion promoter composition using any suitable method. Exemplary methods well-known in the art include, without limitation, spin-coating, curtain coating, spray coating, roller coating, dip coating, and screen printing, among other methods. In the semiconductor manufacturing industry, spin-coating is preferred to take advantage of existing equipment and processes. Preferably, after being disposed on a surface, the solvent is removed prior to the next step. Solvent removal is typically achieved by heating (baking) the substrate, such as by heating at a temperature of 80 to 180° C. for a period of time, such as from 10 to 600 seconds.

After contacting the device substrate with the adhesion promoter composition, a coating composition comprising an oligomer chosen from polyarylene oligomers, poly(cyclic-olefin) oligomers, arylcyclobutene oligomers, vinyl aromatic oligomers, and mixtures thereof is disposed on the treated surface. Such composition may be disposed on the substrate using any of the above-described methods for disposing the adhesion promoter on the substrate. Typically, the coating composition comprises one or more oligomers, one or more organic solvents, and optionally one or more additional components such as curing agents, coating enhancers, and the like.

A wide variety of polyarylene oligomers may be used in the present invention. As used herein, the term "polyarylenes" includes polyarylene ethers. Suitable polyarylene oligomers may be synthesized from precursors such as ethynyl aromatic compounds of the formula:

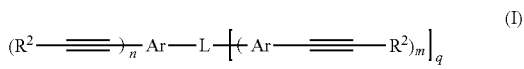

wherein each Ar is an aromatic group or inertly-substituted aromatic group: each $R^2$ is independently hydrogen, an alkyl, aryl or inertly-substituted alkyl or aryl group; L is a covalent bond or a group which links one Ar to at least one other Ar; n and m are integers of at least 2; and q is an integer of at least 1. As such, the ethynyl aromatic compounds typically have four or more ethynyl groups (for example, tetraethynyl aromatic compounds).

Suitable polyarylene oligomers used in the temporary bonding compositions may comprise a polymer comprising as polymerized units:

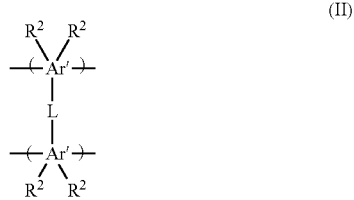

wherein Ar' is the residual of the reaction of product of $(C\equiv C)_n$—Ar or Ar—$(C\equiv C)_m$ moieties and $R^2$, L, n and m are as defined above. Polyarylene copolymers useful in the invention include as polymerized units a monomer having the formula:

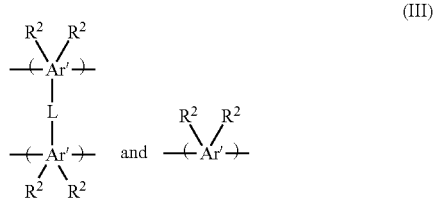

wherein Ar' and $R^2$ are as defined above.

Exemplary polyarylenes include, but are not limited to, those wherein Ar-L-Ar is: biphenyl; 2,2-diphenyl propane; 9,9'-diphenyl fluorene; 2,2-diphenyl hexafluoro propane; diphenyl sulfide; oxydiphenylene; diphenyl ether; bis(phenylene)diphenylsilane; bis(phenylene)phosphine oxide; bis(phenylene)benzene; bis(phenylene)naphthalene; bis(phenylene)anthracene; thiodiphenylene; 1,1,1-triphenyleneethane; 1,3,5-triphenylenebenzene; 1,3,5-(2-phenylene-2-propyl)benzene; 1,1,1-triphenylenemethane; 1,1,2,2-tetraphenylene-1,2-diphenylethane; bis(1,1-diphenylenethyl)benzene; 2,2'-diphenylene-1,1,1,3,3,3-hexafluoropropane; 1,1-diphenylene-1-phenylethane; naphthalene; anthracene; or bis(phenylene)napthacene; more preferably biphenylene; naphthylene; p,p'-(2,2-diphenylene propane) (or —C$_6$H$_4$—C(CH$_3$)$_2$—C$_6$H$_4$—); p,p'-(2,2-diphenylene-1,1,1,3,3,3hexafluoropropene) and (—C$_6$H$_4$—C(CF$_3$)$_2$—C$_6$H$_4$—). Useful bis-phenyl derivatives include 2,2-diphenyl propane; 9,9'-diphenyl fluorene; 2,2-diphenyl hexafluoro propane; diphenyl sulfide; diphenyl ether; bis(phenylene)diphenylsilane; bis(phenylene)phosphine oxide; bis(phenylene)benzene; bis(phenylene)naphthalene; bis(phenylene)anthracene; or bis(phenylene)napthacene.

The polyarylene precursor monomers may be prepared by a variety of methods known in the art, such as by: (a) selectively halogenating, preferably brominating, a polyphenol (preferably a bisphenol) preferably in a solvent, where each phenolic ring is halogenated with one halogen on one of the two positions ortho to the phenolic hydroxyl group; (b) converting the phenolic hydroxyl on the resulting poly(ortho-halophenol), preferably in a solvent, to a leaving group such as a sulfonate ester (for example, a trifluoromethanesulfonate ester prepared from trifluoromethanesulfonyl halide or trifluoromethane sulfonic acid anhydride) which is reactive with and replaced by terminal ethynyl compounds; and (c) reacting the reaction product of step (b) with an ethynyl-containing compound or an ethynyl synthon in the presence of an aryl ethynylation, preferably palladium, catalyst and an acid acceptor to simultaneously replace the halogen and the trifluoromethylsulfonate with an ethynyl-containing group (for example, acetylene, phenylacetylene, substituted phenylacetylene or substituted acetylene). Further explanation of this synthesis is provided in Int. Pat. App. WO 97/10193 (Babb).

The ethynyl aromatic monomers of Formula (I) are useful to prepare polymers of either Formula (II) or (III). Polymerization of the ethynyl aromatic monomers is well within the ability of one skilled in the art. While the specific conditions of polymerization are dependent on a variety of factors including the specific ethynyl aromatic monomer(s) being polymerized and the desired properties of the resulting polymer, in general, the conditions of polymerization are detailed in Int. Pat. App. WO 97/10193 (Babb).

Particularly suitable polyarylenes for use in the present invention include those sold as SiLK™ Semiconductor Dielectric (available from Dow Electronic Materials, Marlborough, Mass.). Other particularly suitable polyarylenes include those disclosed in WO 00/31183, WO 98/11149, WO 97/10193, WO 91/09081, EP 755 957, and U.S. Pat. Nos. 5,115,082; 5,155,175; 5,179,188; 5,874,516; and 6,093,636.

Suitable cyclic-olefin materials are poly(cyclic-olefins), which may be thermoplastic, and preferably have a weight average molecular weight ($M_w$) of from 2000 to 200,000 Daltons, more preferably from 5000 to 100,000 Daltons, and even more preferably from 2000 to 50,000 Daltons. Preferred poly(cyclic-olefins) have a softening temperature (melt viscosity at 3,000 PaS) of at least 100° C., and more preferably at least 140° C. Suitable poly(cyclic-olefins) also preferably have a glass transition temperature ($T_g$) of at least 60° C., more preferably from 60 to 200° C., and most preferably from 75 to 160° C.

Preferred poly(cyclic-olefins) are comprised of recurring monomers of cyclic-olefins and acyclic olefins, or ring-opening polymers based on cyclic-olefins. Suitable cyclic olefins for use in the present invention are chosen from norbornene-based olefins, tetracyclododecene-based olefins, dicyclopentadiene-based olefins, and derivatives thereof. Derivatives include alkyl (preferably $C_1$-$C_{20}$ alkyls, more preferably $C_1$-$C_{10}$ alkyls), alkylidene (preferably $C_1$-$C_{20}$ alkylidenes, more preferably $C_1$-$C_{10}$ alkylidenes), aralkyl (preferably $C_6$-$C_{30}$ aralkyls, more preferably $C_6$-$C_{18}$ aralkyls), cycloalkyl (preferably $C_3$-$C_{30}$ cycloalkyls, more preferably $C_3$-$C_{18}$ cycloalkyls), ether, acetyl, aromatic, ester, hydroxy, alkoxy, cyano, amide, imide, and silyl-substituted derivatives. Particularly preferred cyclic-olefins for use in the present invention include those chosen from

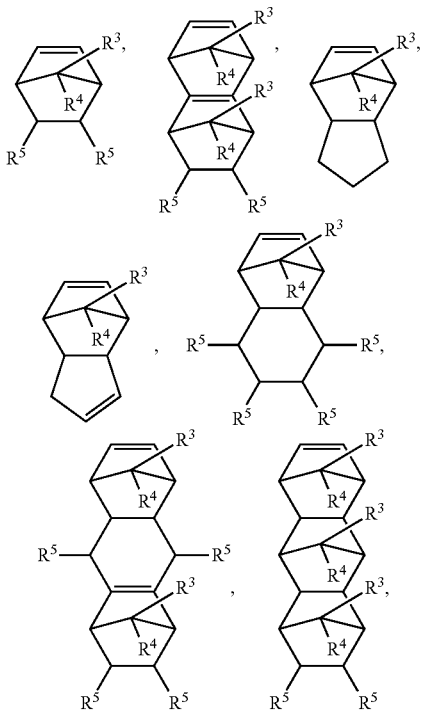

and combinations of the foregoing, where each $R^3$ and $R^4$ is independently chosen from H, and alkyl groups (preferably $C_1$-$C_{20}$ alkyls, more preferably $C_1$-$C_{10}$ alkyls), and each $R^5$ is independently chosen from H, substituted and unsubstituted aryl groups (preferably $C_6$-$C_{18}$ aryls), alkyl groups (preferably $C_1$-$C_{20}$ alkyls, more preferably $C_1$-$C_{10}$ alkyls), cycloalkyl groups (preferably $C_3$-$C_{30}$ cycloalkyl groups, more preferably $C_3$-$C_{18}$ cycloalkyl groups), aralkyl groups (preferably $C_6$-$C_{30}$ aralkyls, more preferably $C_6$-$C_{18}$ aralkyl groups such as benzyl, phenethyl, phenylpropyl, and the like), ester groups, ether groups, acetyl groups, alcohols (preferably $C_1$-$C_{10}$ alcohols), aldehyde groups, ketones, nitriles, and combinations thereof.

Preferred acyclic olefins are chosen from branched and unbranched $C_2$-$C_{20}$ alkenes (preferably $C_2$-$C_{10}$ alkenes). More preferably, the acyclic olefins have the structure $(R^6)_2C=C(R^6)_2$, where each $R^6$ is independently chosen from H and alkyl groups (preferably $C_1$-$C_{20}$ alkyls, more preferably $C_1$-$C_{10}$ alkyls). Particularly preferred acyclic olefins for use in the present invention include those chosen from ethene, propene, and butene, with ethene being the most preferred.

Methods of producing cyclic-olefin copolymers are known in the art. For example, cyclic-olefin copolymers can be produced by chain polymerization of a cyclic monomer with an acyclic monomer. When norbornene is reacted with ethene under such conditions, an ethene-norbornene copolymer containing alternating norbornanediyl and ethylene units is obtained. Examples of copolymers produced by this method include those available under the TOPAS™ (available from Topas Advanced Polymers) and APEL™ (produced by Mitsui Chemicals) brands. A suitable method for making these copolymers is disclosed in U.S. Pat. No. 6,008,298. Cycloolefin copolymers can also be produced by ring-opening metathesis polymerization of various cyclic monomers followed by hydrogenation. The polymers resulting from this type of polymerization can be thought of conceptually as a copolymer of ethene and a cyclic-olefin monomer (such as alternating units of ethylene and cyclopentane-1,3-diyl). Examples of copolymers produced by this ring-opening method include those provided under the ZEONOR™ (from Zeon Chemicals) and ARTON™ (from JSR Corporation) brands. A suitable method of making these copolymers by this ring-opening method is disclosed in U.S. Pat. No. 5,191,026.

Arylcyclobutene oligomers are well-known in the art. Suitable arylcyclobutene oligomers include, but are not limited to, those having the formula:

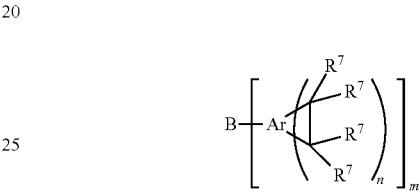

wherein B is an n-valent linking group; Ar is a polyvalent aryl group and the carbon atoms of the cyclobutene ring are bonded to adjacent carbon atoms on the same aromatic ring of Ar; m is an integer of 1 or more; n is an integer of 1 or more; and $R^7$ is a monovalent group. Preferably, the polyvalent aryl group, Ar, may be composed of 1-3 aromatic carbocyclic or heteroaromatic rings. It is preferred that the aryl group comprise a single aromatic ring, and more preferably a phenyl ring. The aryl group is optionally substituted with 1 to 3 groups chosen from ($C_1$-$C_6$)alkyl, tri($C_1$-$C_6$)alkylsilyl, ($C_1$-$C_6$)alkoxy, and halo, preferably with one or more of ($C_1$-$C_6$) alkyl, tri($C_1$-$C_3$)alkylsilyl, ($C_1$-$C_3$)alkoxy, and chloro, and more preferably with one or more of ($C_1$-$C_3$)alkyl, tri($C_1$-$C_3$) alkylsilyl, and ($C_1$-$C_3$)alkoxy. It is preferred that the aryl group is unsubstituted. It is preferred that n=1 or 2, and more preferably n=1. Preferably, m=1-4, more preferably m=2-4, and yet more preferably m=2. It is preferred that $R^7$ is chosen from H and ($C_1$-$C_6$)alkyl, and more preferably from H and ($C_1$-$C_3$)alkyl. Preferably, B comprises one or more carbon-carbon double bonds (ethylenic unsaturation). Suitable single valent B groups preferably have the formula —[C($R^8$)=CR$^9$]$_x$Z$^1$, wherein $R^8$ and $R^9$ are independently chosen from hydrogen, ($C_1$-$C_6$)alkyl, and aryl; $Z^1$ is chosen from hydrogen, ($C_1$-$C_6$)alkyl, aryl, siloxanyl, —CO$_2$R$^{10}$; each $R^{10}$ is independently chosen from H, ($C_1$-$C_6$)alkyl, aryl, aralkyl, and alkaryl; and x=1 or 2. Preferably, $R^8$ and $R^9$ are independently chosen from H, ($C_1$-$C_3$)alkyl, and aryl, and more preferably H and ($C_1$-$C_3$)alkyl. It is preferred that $R^{10}$ is ($C_1$-$C_3$) alkyl, aryl, and aralkyl. $Z^1$ is preferably siloxyl. Preferred siloxyl groups have the formula —[Si($R^{11}$)$_2$—O]p-Si($R^{11}$)$_2$—, wherein each $R^{11}$ is independently chosen from H, ($C_1$-$C_6$)alkyl, aryl, aralkyl, and alkaryl; and p is an integer from 1 or more. It is preferred that $R^{11}$ is chosen from ($C_1$-$C_3$)alkyl, aryl, and aralkyl. Suitable aralkyl groups include benzyl, phenethyl and phenylpropyl.

Preferably, the arylcyclobutene oligomers comprise one or more oligomers of the formula:

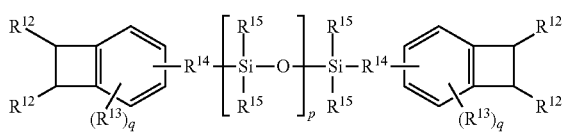

wherein each $R^{12}$ is independently chosen from H and $(C_1-C_6)$alkyl, and preferably from H and $(C_1-C_3)$alkyl; each $R^{13}$ is independently chosen from $(C_1-C_6)$alkyl, tri$(C_1-C_6)$alkylsilyl, $(C_1-C_6)$alkoxy, and halo; each $R^{14}$ is independently a divalent, ethylenically unsaturated organic group; each $R^{15}$ is independently chosen from H, $(C_1-C_6)$alkyl, aralkyl and phenyl; p is an integer from 1 or more; and q is an integer from 0-3. Each $R^{12}$ is preferably independently chosen from H and $(C_1-C_3)$alkyl, and more preferably each $R^{12}$ is H. It is preferred that each $R^{13}$ is independently chosen from $(C_1-C_6)$alkyl, tri$(C_1-C_3)$alkylsilyl, $(C_1-C_3)$alkoxy, and chloro, and more preferably from $(C_1-C_3)$alkyl, tri$(C_1-C_3)$alkylsilyl, and $(C_1-C_3)$alkoxy. Preferably, each $R^{14}$ is independently chosen from a $(C_2-C_6)$alkenyl, and more preferably each $R^{14}$ is —CH=CH—. Each $R^{15}$ is preferably chosen from $(C_1-C_3)$ alkyl, and more preferably each $R^{15}$ is methyl. Preferably, p=1-5, more preferably p=1-3, and yet more preferably p=1. It is preferred that q=0. A particularly preferred arylcyclobutene oligomer, 1,3-bis(2-bicyclo[4.2.0]octa-1,3,5-trien-3-yl ethenyl)-1,1,3,3 tetramethyldisiloxane ("DVS-bis-BCB"), has the formula

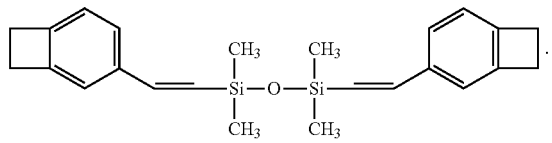

Arylcyclobutene oligomers may be prepared by any suitable means, such as those described in U.S. Pat. Nos. 4,812,588; 5,136,069; 5,138,081; and Int. Pat. App. No. WO 94/25903. Suitable arylcyclobutene oligomers are also commercially available under the CYCLOTENE™ brand, available from Dow Electronic Materials. The arylcyclobutene oligomers may be used as is, or may be further purified by any suitable means.

Vinyl aromatic oligomers are well-known in the art. Such vinyl aromatic oligomers include oligomers of only vinyl aromatic monomers and oligomers of vinyl aromatic monomers with one or more reactive ethylenically unsaturated co-monomers. Preferably, the vinyl aromatic monomers contain one vinyl group. Suitable vinyl aromatic monomers are unsubstituted vinyl aromatic monomers and substituted vinyl aromatic monomers where one or more hydrogens are replaced with a substituent group selected from the group of $(C_1-C_6)$alkyl, $(C_1-C_6)$alkoxy, halo, and amino Exemplary vinyl aromatic monomers include, without limitation, styrene, vinyltoluene, vinylxylene, vinylanisole, vinyldimethoxybenzene, vinylaniline, halostyrene such as fluorostyrene, α-methylstyrene, β-methoxystyrene, ethylvinylbenzene, vinylpyridines, vinylimidazoles, vinylpyrroles, and mixtures thereof. Preferred vinyl aromatic monomers are styrene, vinyltoluene, vinylxylene, vinylanisole, ethylvinylbenzene, and mixtures thereof. Preferred reactive co-monomers are those comprising a reactive moiety, that is, a moiety capable of further polymerization (or crosslinking) following formation of the vinyl aromatic oligomer, such as an allyl moiety or a vinyl group, in addition to an olefinic (or ethylenically unsaturated) moiety used to for the vinyl aromatic oligomer. More preferably, the reactive co-monomers comprise an allyl moiety in addition to the ethylenic unsaturation used to form the vinyl aromatic oligomer, and even more preferably comprise an allyl ester moiety in addition to the ethylenic unsaturation. Exemplary reactive co-monomers useful in forming the vinyl aromatic oligomers include, but are not limited to, vinylcyclohexene, vinyl ethers, asymmetrical dienes or trienes such as terpene monomers (e.g. limonene or myrcene), diallyl maleate, allyl acrylate, allyl methacrylate, allyl cinnamate, diallyl fumerate, allyl tiglate, divinylbenzene, and mixtures thereof. Preferred reactive co-monomers are diallyl maleate, allyl acrylate, allyl methacrylate allyl cinnamate, allyl fumerate, and mixtures thereof, and more preferably diallyl maleate, allyl methacrylate and mixtures thereof. It will be appreciated by those skilled in the art that one or more secondary co-monomers may also be used to form the vinyl aromatic oligomers. Such secondary co-monomers are ethylenically unsaturated, but do not contain a reactive moiety. Exemplary secondary co-monomers include, but are not limited to, (meth)acrylic acid, (meth)acrylamides, $(C_1-C_{10})$alkyl(meth)acrylates, aromatic(meth)acrylates, substituted ethylene monomers, and poly(alkylene oxide) monomers.

The molar ratio of vinyl aromatic monomers to co-monomers in such vinyl aromatic oligomers is preferably from 99:1 to 1:99, more preferably from 95:5 to 5:95, and still more preferably from 90:10 to 10:90. Such vinyl aromatic oligomers may be prepared by any suitable method, such as any of those known in the art. Typically, vinyl aromatic oligomers are prepared by free-radical polymerization of a vinyl aromatic monomer and a co-monomer. Preferred vinyl aromatic oligomers comprise unreacted allyl moieties that allow such oligomers to further cure.

The coating compositions are prepared by combining one or more oligomers as described above with one or more organic solvents, and one or more optional components. It is preferred that the oligomer is an arylcyclobutene oligomer. Suitable organic solvents include those described above for use in the adhesion promoter compositions. Exemplary optional components in the coating compositions include one or more curing agents, one or more anti-oxidants, and the like. Curing agents may aid in the curing of the oligomers, and may be activated by heat or light. Suitable curing agents include thermally generated initiators and photoinitiators. The selection of such curing agents is well within the ability of those skilled in the art. The amount of the oligomers, solvents and optional components in the coating composition may vary across a wide range and is within the ability of one skilled in the art. It will be appreciated by those skilled in the art that the solids content in the coating compositions may be adjusted, along with the spin speed, to achieve a desired thickness of the coating composition on the adhesion promoter treated surface.

The coating compositions may be disposed (or coated) on the adhesion promoted device substrate surface by any suitable method, such as those described above for disposing the adhesion promoter on the device substrate. Such methods of depositing coating compositions are well-known in the art. After being disposed on an adhesion promoted surface, the coating compositions are typically cured using the appropriate method for the oligomer selected. Such curing methods are well-known in the art. For example, arylcyclobutene oligomers may be cured by heating, or in the case of photodefinable arylcyclobutene oligomers by exposure to actinic radiation (light) of an appropriate wavelength.

Also provided by the present invention is a self-priming coating composition comprising a poly(alkoxysilane) hydrolyzed with ≤1 mole % of water, an oligomer chosen from polyarylene oligomers, poly(cyclic-olefin) oligomers, arylcyclobutene oligomers, vinyl aromatic oligomers, and mixtures thereof, and an organic solvent, wherein the composition comprises ≤1 mole % of alcohol of hydrolysis. Optionally, these self-priming compositions may comprise one or more additional components such as anti-oxidants, photo-cross-linking agents, and coating enhancers. Such optional components are well-known to those skilled in the art. Any of the poly(alkoxysilanes) described above may be used in this composition. Any of the oligomers described above for the coating composition may be used in this self-priming composition, and preferably the oligomer is an arylcyclobutene oligomer. Suitable organic solvents are those described above for use in the adhesion promoter compositions. As used herein, the term "self-priming coating composition" refers to a composition comprising both an adhesion promoting poly(alkoxysilane) hydrolyzed with ≤1 mole % of water and a coating oligomer, and preferably also comprising an organic solvent. An advantage of these self-priming coating compositions is that a separate step of applying an adhesion promoter can be avoided. Alternatively, these self-priming coating compositions may be used to form a first layer coating layer, upon which subsequent coating layers are deposited. In certain applications, the use of a self-priming coating composition is preferred over the use of a separate adhesion promoter composition. Such self-priming compositions may suitably be used to form dielectric coatings, photodefinable coatings, temporary adhesives, permanent adhesives, and the like.

The amounts of the poly(alkoxysilane) hydrolyzed with ≤1 mole % of water, coating oligomer, and solvent employed in the self-priming coating composition depends upon a number of factors including the specific end-use application and the properties desired. If the self-priming coating composition is intended to have one or more coating oligomer layers subsequently applied to it, the self-priming coating composition will typically contain lesser amounts of the coating oligomer than when no subsequent coating oligomer layer is used. In general, regardless of its intended end-use, the self-priming coating composition comprises from 0.01 to 10 wt % poly(alkoxysilane) hydrolyzed with ≤1 mole % water, from 10 to 99.98 wt % solvent, and from 0.01 to 90 wt % coating oligomer, where the weight percents are based on the total weight of the composition. Preferably, the self-priming coating compositions comprise form 0.01 to 5 wt % of poly(alkoxysilane) hydrolyzed with ≤1 mole % of water, more preferably from 0.01 to 3 wt %, and even more preferably from 0.01 to 2 wt %. When subsequent coating oligomer compositions will be disposed on the self-priming composition, it is preferred that the coating oligomers in the self-priming coating compositions are present in an amount of from 0.01, more preferably from 1, and even more preferably from 2 wt % to 20, more preferably 10, and even more preferably 5 wt %. When subsequent coating oligomer compositions will not be disposed on the self-priming coating, it is preferred that the coating oligomer be present in the composition in an amount of from 5, more preferably from 10, and yet more preferably from 20 wt % to 90, more preferably to 80, and still more preferably to 65 wt %. Preferred amounts of solvent vary from 10 to 98 wt %, more preferably from 20 to 90 wt %, and still more preferably from 20 to 75 wt %. In one embodiment, the composition comprises from 0.01 to 10 wt % of poly(alkoxysilane) hydrolyzed with ≤1 mole % water, from 40 to 99.5 wt % of solvent; and from 1 to 80 wt % of coating oligomer, based on the total weight of the composition; wherein the composition comprises ≤1 mole % of alcohol of hydrolysis. In another embodiment, the composition comprises from 0.01 to 10 wt % of poly(alkoxysilane) hydrolyzed with ≤1 mole % of water, from 10 to 99.9 weight percent of solvent, and from 0.01 to 90 percent by weight of coating oligomer, based on the total weight of the composition wherein the composition comprises ≤1 mole % of alcohol of hydrolysis.

The self-priming coating compositions may be disposed on a device substrate to form a coated film using any of the methods described above for the adhesion promoting compositions. Spin-coating is a preferred method. Following deposition on a device substrate, the coated film is typically cured, such as by heating, exposure to actinic radiation (light), or a combination thereof. Photodefineable arylcyclobutenes are typically photocrosslinked prior to further cure. The specific curing conditions used depend on the particular oligomer selected, the particular application such as whether the coated film is a dielectric or an adhesive, as well as on other parameters known to those skilled in the art.

Dynamic light scattering is a technique for determining the size distribution profile of small particles in a suspension and can be used as a facile method to monitor the degree of hydrolysis of alkoxysilanes. Conventional hydrolysis of alkoxysilane adhesion promoters, particularly uncontrolled hydrolysis, leads to formation of components in the composition having mean particle sizes >>2 nm as determined by dynamic light scattering, and typically such components have mean particle sizes >10 nm. The low level of hydrolysis of the poly(alkoxysilanes) of the present invention results in components having mean particle sizes <<10 nm, typically ≤2 nm, and preferably ≤1 nm, as determined by conventional dynamic light scattering techniques. Preferably, the present poly(alkoxysilanes) hydrolyzed with ≤1 mole % water have a mean particle size of ≤2 nm, and more preferably ≤1 nm. It is also preferred that the present compositions have a unimodal particle size distribution. Hydrolyzed alkoxysilanes having a mean particle size distribution of >1 nm do not provide adequate adhesion for many applications, such as when used with imagable dielectrics.

EXAMPLE 1

Bis[3-(trimethoxysilyl)propyl]amine (0.41 g), of [3-(2-aminoethylamino)propyl]-trimethoxysilane (0.21 g), and 99.38 g of 4-methyl-2-pentanol containing 400 ppm water were combined in a 200 mL bottle. The mixture was stirred with a magnetic stirrer at ambient temperature (23° C.) in order to effect hydrolysis. Hydrolysis proceeded such that a single phase solution is produced in 15 minutes.

COMPARATIVE EXAMPLE 1

Vinyltrimethoxysilane (0.3 g) and 99.7 g of 1-methoxy-2-propanol containing 800 ppm water were combined in a 200 ml bottle. The mixture was stirred using a magnetic stirrer at ambient temperature (23° C.) in order to effect hydrolysis. Hydrolysis proceeded such that a single phase solution was produced in 15 minutes.

COMPARATIVE EXAMPLE 2

3-Aminopropyltriethoxylsilane (0.1 g) and 99.9 g of 1-Methoxy-2-propanol containing 800 ppm water were combined in a 200 mL bottle. The mixture is stirred magnetically at ambient temperature (23° C.) in order to effect hydrolysis. Hydrolysis proceeded such that a single phase solution was produced in 15 minutes.

COMPARATIVE EXAMPLE 3

[3-(2-Aminoethylamino)propyl]trimethoxysilane (0.6 g) and 99.4 g of 1-methoxy-2-propanol containing 800 ppm water were combined in a 200 mL bottle. The mixture was stirred using a magnetic stirrer at ambient temperature (23° C.) in order to effect hydrolysis. Hydrolysis proceeded such that a single phase solution was produced in 15 minutes.

EXAMPLE 2

Bis[3-(trimethoxysilyl)propyl]amine (0.6 g), and 99.4 g of 4-methyl-2-pentanol containing 400 ppm water were combined in a 200 mL bottle. The mixture was stirred using a magnetic stirrer at ambient temperature (23° C.) in order to effect hydrolysis. Hydrolysis proceeded such that a single phase solution was produced in 15 minutes.

EXAMPLE 3

Bis[3-(triethoxysilyl)propyl]amine (0.5 g) and 99.5% of 4-methyl-2-pentanol containing 400 ppm water were combined in a 200 mL bottle. The mixture was stirred using a magnetic stirrer at ambient temperature (23° C.) in order to effect hydrolysis. Hydrolysis proceeded such that a single phase solution was produced in 15 minutes.

EXAMPLE 4

Bis[3-(triethoxysilyl)propyl]amine (0.5 g) and 99.5% of 1-methoxy-2-propanol containing 800 ppm water were combined in a 200 mL bottle. The mixture was stirred using a magnetic stirrer at ambient temperature (23° C.) in order to effect hydrolysis. Hydrolysis proceeded such that a single phase solution was produced in 15 minutes.

EXAMPLE 5

Benzocyclobutene bis(3-(triethoxylsilyl)propyl)acrylamide (0.5 g) and 99.5 g of 1-methoxy-2-propanol containing 500 ppm water were combined in a 200 mL bottle. The mixture was stirred using a magnetic stirrer at ambient temperature (23° C.) in order to effect hydrolysis. Hydrolysis proceeded such that a single phase solution was produced in 15 minutes.

EXAMPLE 6

$N^1,N^1$-Bis(3-(trimethoxysilyl)propyl)ethane-1,2-diamine (0.5 g) is combined with 2-methyl-1-butanol containing 350 ppm water in a 200 mL bottle. The mixture is stirred at ambient temperature (23° C.) in order to effect hydrolysis.

EXAMPLE 7

To a 200 mL bottle are combined 4 methyl-2-pentanol containing 250 ppm water and 3-(trimethoxysilyl)-N-(2-(trimethyoxysilyl)ethyl)-N-(3-(trimethoxysilyl)propyl)propan-1-amine. The mixture is stirred at ambient temperature (23° C.) in order to effect hydrolysis.

EXAMPLE 8

To a 200 mL bottle are combined 4 methyl-2-pentanol containing 400 ppm water and bis(3,3,9,9-tetramethoxy-2,10-dioxa-3,9-disilaundecan-6-yl)amine. The mixture is stirred at ambient temperature (23° C.) in order to effect hydrolysis.

EXAMPLE 9

The adhesion promoting compositions from Examples 1-5 and Comparative Examples 1-3 were evaluated using a lithographic printing adhesion test. Each adhesion promoter composition was coated on a 200 mm test wafer using a Site Trac TT5-XP coater at a spin speed of 2000 rpm for 40 seconds followed by a 90° C. bake for 90 seconds to ensure solvent removal. An oligomer composition comprising 40% of an aqueous developable benzocyclobutene oligomer, which is a copolymer of DVS-bisBCB and benzocyclobutene acrylic acid having a molecular weight of approximately 5000, in a mixture of PROGLYDE™ DMM, PGMEA and anisole and containing a trifunctional diazonapthoquinone photoactive compound (CYCLOTENE™ P6505, available from The Dow Chemical Company, Midland, Mich.) was coated on top of the adhesion promoter layer using a Site Trace TT6-XP coater at a spin speed around 1500 rpm to target a film thickness of approximately 6.5 μm. The oligomer composition was nexted baked at 90° C. for 90 seconds to ensure solvent removal. Next, each oligomer-coated wafer was exposed on an ASML 2001-line stepper using a bright field reticle to print rows of variously sized posts (from 1 to 25 μm) on the wafer. After exposure, a 15 minute post exposure hold was utilized to allow moisture diffusion back into the film. Next, the exposed areas of the oligomer resin were developed on a Site Trac TTP-X5 tool using a CD-26 developer solution employing a 60 second single puddle followed by a 90 second de-ionized water rinse. The post pattern remaining on the wafer was evaluated under an optical microscope. A sample was considered to pass the lithographic adhesion test when the minimum feature size of the remaining posts after development was less than or equal to 5 μm. The data are reported in Table 1 below.

EXAMPLE 10

Dynamic light scattering measurements were carried out using a Malvern Zetasizer Nano ZS instrument. A sample of an adhesion promoter solution (1.5 mL) was transferred to a quartz cuvette, and then the cuvette was inserted in the sample holder of the Zetasizer instrument. The instrument software was set up for size measurement, and 15 to 24 scans were normally required to obtain an accurate particle size distribution for each sample. The mean particle sizes determined for Examples 1-5 and Comparative Examples 1-3 are reported in Table 1 below. Each of the adhesion promoters of the invention had only a single peak (unimodal distribution) with a mean particle size of <1 nm. Each of the comparative examples had at least one peak with a mean particle size >1 nm. Comparative Example 1 had 2 peaks (bimodal distribution), with one distribution having a mean particle size of >10 nm. Such large mean particle sizes in the comparative examples indicates the formation of larger nanoparticles due to the larger amount of silane hydrolysis, as compared to the poly(alkoxysilanes) of the invention.

TABLE 1

| Formulation | Adhesion to silicon | Lithographic Printing Adhesion Test - Post Size Remaining (μm) | Mean Particle Size (nm) |
|---|---|---|---|
| Comparative Example 1 | Poor | No posts remaining | <1, >10 bimodal |
| Comparative Example 2 | Poor | No posts remaining | 3-5 |
| Comparative Example 3 | Poor | 15 | >1 |
| Example 1 | Good | 3 | <1 |
| Example 2 | Good | 3 | <1 |
| Example 3 | Good | 2 | <1 |
| Example 4 | Good | 2 | <1 |
| Example 5 | Good | 2 | <1 |

EXAMPLE 11

The adhesion promoting compositions from Examples 1-5 and Comparative Examples 1-3 were evaluated according to the Cross-Hatch/Tape Peel test (ASTM D 3359) using a PA-2000 kit from Gardco. The cross hatch was applied and excess debris removed using a steady stream of compressed dry air prior to tape peel. After tape peel, the adhesion was evaluated and each of the adhesion promoting compositions from Examples 1-5 and Comparative Examples 1-3 were found to pass with 0% removed.

EXAMPLE 12

A temporary bonding coating composition was prepared by combining 83.63 g of 68.5% DVS-bisBCB oligomer (having an average molecular weight of 25,000-30,000) in Proglyde™ DMM solvent was added 8.78 g of poly(tetramethylene glycol) having a molecular weight of 2900, (available as PolyTHF 2900, from BASF), 4.17 g of BAC-45 (a diacrylate terminated butadiene rubber having a molecular weight of 3000), 0.68 g of dicumyl peroxide, 0.49 g of a commercial antioxidant, and 2.25 g of Proglyde™ DMM solvent. The composition was manually mixed with a wooden stick, heated to 50° C. for approximately 1 hour, and then rolled until homogeneous.

200 mm silicon wafers were subjected to an oxygen plasma etch for 10 seconds. Next, 2 mL of the adhesion promoter from Example 4 was spin coated on the attachment surface of a carrier wafer (2000 rpm, 30 seconds), followed by a soft bake at 120° C. for 90 seconds, followed by cooling. The temporary bonding coating composition was spin coated (2000 rpm) on a device wafer, soft baked at 120° C. for 90 seconds, cooled for 30 seconds, and soft baked at 160° C. for 120 seconds to form a layer of a temporary bonding composition on the device wafer. The carrier wafer was then vacuum laminated to the temporary bonding coating composition at 80° C. for 60 seconds, with vacuum applied for 45 seconds and pressure applied for 60 seconds. The laminated wafers were then cured by heating on a hot plate, device side down, for 120 seconds at 210° C., in a nitrogen atmosphere. The thickness of the cured temporary bonding layer was approximately 25 μm. Following curing, the wafers were successfully debonded with a razor blade inserted near a notch and guided around the wafer, with the device wafer separating from the temporary bonding composition. The temporary bonding composition remained adhered to the adhesion promoted attachment surface of the carrier wafer.

EXAMPLE 13

The procedure of Example 12 was repeated except that the temporary bonding coating composition also contained 41.82 g of a 90/10 styrene:diallyl maleate oligomer. The coating composition contained DVS-bisBCB oligomer and styrene:diallyl maleate oligomer in a weight ratio of 1:1. The thickness of the cured temporary bonding layer from this composition was approximately 26 μm. Following curing, the wafers were successfully debonded with a razor blade inserted near a notch and guided around the wafer, with the device wafer separating from the temporary bonding composition. The temporary bonding composition remained adhered to the adhesion promoted attachment surface of the carrier wafer.

EXAMPLE 14

The procedure of Example 12 was repeated except that the DVS-bisBCB oligomer was replaced with 83.63 g of a 90/10 styrene:diallyl maleate oligomer in Proglyde™ DMM solvent (68.5% solids). This coating composition contained no DVS-bisBCB oligomer. The thickness of the cured temporary bonding layer from this composition was approximately 36 μm. Following curing, the wafers were successfully debonded with a razor blade inserted near a notch and guided around the wafer, with the device wafer separating from the temporary bonding composition. The temporary bonding composition remained adhered to the adhesion promoted attachment surface of the carrier wafer.

What is claimed is:

1. A process for manufacturing a device, comprising:
   providing a device substrate having a surface to be coated;
   treating the surface to be coated with an adhesion promoting composition comprising an poly(alkoxysilane) having from 2 to 6 alkoxysilane moieties and a solvent, wherein the poly(alkoxysilane) is hydrolyzed with ≤1 mole % of water, and wherein the composition comprises ≤1 mole % of alcohol of hydrolysis; and
   disposing a coating composition comprising an oligomer chosen from polyarylene oligomers, poly(cyclic-olefin) oligomers, arylcyclobutene oligomers, vinyl aromatic oligomers, and mixtures thereof on the treated surface.

2. The process of claim 1 wherein the device substrate is an electronic device substrate.

3. The process of claim 2 wherein the electronic device substrate comprises a surface comprising one or more of silicon, glass, ceramic, and metal.

4. The process of claim 1 wherein the poly(alkoxysilane) prior to being hydrolyzed has the formula:

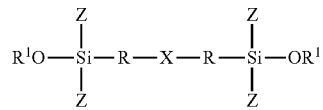

wherein each R is independently chosen from $(C_1$-$C_6)$alkylidene, $(C_1$-$C_6)$alkylene, $(C_6$-$C_{10})$arylene, and $(C_2$-$C_6)$alkenylene; each $R^1$ is independently chosen from H, $(C_1$-$C_6)$ alkyl and $(C_1$-$C_6)$acyl; each Z is independently chosen from $(C_1$-$C_6)$alkyl, $(C_2$-$C_6)$alkenyl and —$OR^1$; X=$(C_6$-$C_{10})$ arylene, O, S, S—S, S—S—S, S—S—S—S, N(Y), P(Y), or a covalent bond; Y=H, $(C_1$-$C_6)$alkyl, $(C_1$-$C_6)$alkylene-N $(Y^1)_2$, $(C_2$-$C_6)$alkenyl, $(C_1$-$C_6)$alkylene-Si$(Z)_2(OR^1)$, or aryl (meth)acryloyl; and $Y^1$=H, $(C_1$-$C_6)$alkyl, or $(C_2$-$C_6)$alkenyl; wherein each R is optionally substituted with one or more of $(C_1$-$C_6)$alkylidene-Si$(Z)_2(OR^1)$ and $(C_1$-$C_6)$alkylene-Si$(Z)_2$ $(OR^1)$.

5. The process of claim 1 wherein the poly(alkoxysilane) is hydrolyzed with ≤0.5 mole % of water.

6. The process of claim 1 wherein the arylcyclobutane oligomer has the formula:

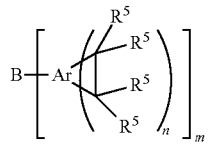

wherein B is an n-valent linking group; Ar is a polyvalent aryl group and the carbon atoms of the cyclobutene ring are bonded to adjacent carbon atoms on the same aromatic ring of Ar; m is an integer of 1 or more; n is an integer of 1 or more; and $R^5$ is a monovalent group.

7. The process of claim 1 wherein the adhesion promoting composition has a mean particle size of ≤1 nm, as determined by dynamic light scattering.

8. The process of claim 1 further comprising a step of solvent removal after the treating step and before the step of disposing the coating composition.

9. A process for manufacturing a device, comprising:
providing a device substrate having a surface to be coated;
treating the surface to be coated with an adhesion promoting composition comprising an poly(alkoxysilane) and a solvent, wherein the poly(alkoxysilane) is hydrolyzed with ≤1 mole % of water, and wherein the composition comprises ≤1 mole % of alcohol of hydrolysis; and
disposing a coating composition comprising an oligomer chosen from polyarylene oligomers, poly(cyclic-olefin) oligomers, arylcyclobutane oligomers, vinyl aromatic oligomers, and mixtures thereof on the treated surface;
wherein the poly(alkoxysilane) prior to being hydrolyzed has the formula:

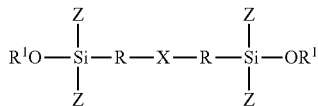

wherein each R is independently chosen from $(C_1-C_6)$ alkylidene, $(C_1-C_6)$alkylene, $(C_6-C_{10})$arylene, and $(C_2-C_6)$alkenylene; each $R^1$ is independently chosen from H, $(C_1-C_6)$alkyl and $(C_1-C_6)$acyl; each Z is independently chosen from $(C_1-C_6)$alkyl, $(C_2-C_6)$alkenyl and —$OR^1$; X=$(C_6-C_{10})$arylene, O, S, S—S, S—S—S, S—S—S—S, N(Y), P(Y), or a covalent bond; Y=H, $(C_1-C_6)$alkyl, $(C_1-C_6)$alkylene-N$(Y^1)_2$, $(C_2-C_6)$alkenyl, $(C_1-C_6)$alkylene-Si$(Z)_2(OR^1)$, or aryl(meth)acryloyl; and $Y^1$=H, $(C_1-C_6)$alkyl, or $(C_2-C_6)$alkenyl; wherein each R is optionally substituted with one or more of $(C_1-C_6)$alkylidene-Si$(Z)_2(OR^1)$ and $(C_1-C_6)$alkylene-Si$(Z)_2(OR^1)$.

10. The process of claim 9 wherein the device substrate is an electronic device substrate.

11. The process of claim 10 wherein the electronic device substrate comprises a surface comprising one or more of silicon, glass, ceramic, and metal.

12. The process of claim 9 wherein the poly(alkoxysilane) is hydrolyzed with ≤0.5 mole % of water.

13. The process of claim 9 wherein the arylcyclobutane oligomer has the formula:

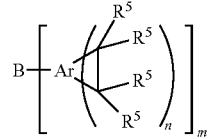

wherein B is an n-valent linking group; Ar is a polyvalent aryl group and the carbon atoms of the cyclobutene ring are bonded to adjacent carbon atoms on the same aromatic ring of Ar; m is an integer of 1 or more; n is an integer of 1 or more; and $R^5$ is a monovalent group.

14. The process of claim 9 wherein the adhesion promoting composition has a mean particle size of ≤1 nm, as determined by dynamic light scattering.

15. The process of claim 9 further comprising a step of solvent removal after the treating step and before the step of disposing the coating composition.

16. A process for manufacturing a device, comprising:
providing a device substrate having a surface to be coated;
treating the surface to be coated with an adhesion promoting composition comprising an poly(alkoxysilane) and a solvent, wherein the poly(alkoxysilane) is hydrolyzed with ≤1 mole % of water, and wherein the composition comprises ≤1 mole % of alcohol of hydrolysis; and
disposing a coating composition comprising an oligomer chosen from polyarylene oligomers, poly(cyclic-olefin) oligomers, arylcyclobutane oligomers, vinyl aromatic oligomers, and mixtures thereof on the treated surface;
wherein the adhesion promoting composition has a mean particle size of ≤1 nm, as determined by dynamic light scattering.

\* \* \* \* \*